(12) United States Patent
Kouwer et al.

(10) Patent No.: US 11,840,705 B2
(45) Date of Patent: Dec. 12, 2023

(54) BIOMIMETIC DOUBLE NETWORK HYDROGELS

(71) Applicant: STICHTING KATHOLIEKE UNIVERSITEIT, Nijmegen (NL)

(72) Inventors: Paul Kouwer, Nijmegen (NL); Alan Rowan, Nijmegen (NL); Maarten Jaspers, Nijmegen (NL); Paula De Almeida, Nijmegen (NL)

(73) Assignee: STICHTING RADBOUD UNIVERSITEIT, Nijmegen (NL)

( * ) Notice: Subject to any disclaimer, the term of this patent is extended or adjusted under 35 U.S.C. 154(b) by 796 days.

(21) Appl. No.: 16/607,824

(22) PCT Filed: Apr. 23, 2018

(86) PCT No.: PCT/EP2018/060348
§ 371 (c)(1),
(2) Date: Oct. 24, 2019

(87) PCT Pub. No.: WO2018/197416
PCT Pub. Date: Nov. 1, 2018

(65) Prior Publication Data
US 2020/0181564 A1    Jun. 11, 2020

(30) Foreign Application Priority Data

Apr. 24, 2017 (EP) .................... 17167774

(51) Int. Cl.
*C12N 5/18* (2006.01)
*C12N 5/00* (2006.01)
(Continued)

(52) U.S. Cl.
CPC .......... *C12N 5/0018* (2013.01); *C08F 120/54* (2013.01); *C08J 3/246* (2013.01);
(Continued)

(58) Field of Classification Search
CPC ............. C12N 5/0018; C12N 2533/40; C12N 2533/54; C08F 120/54; C08J 3/246;
(Continued)

(56) References Cited

U.S. PATENT DOCUMENTS

2011/0182968 A1* 7/2011 Myung .................. A61P 27/02
514/23
2012/0149836 A1* 6/2012 Rowan ............. C08G 65/33348
524/591
(Continued)

FOREIGN PATENT DOCUMENTS

WO  2011007012 A1  1/2011
WO  2015007771 A1  1/2015
WO  2015124732 A1  8/2015

OTHER PUBLICATIONS

Senden et al., Comptes Rendus de l'Académie des Sciences—Series IV—Physics, vol. 1, No. 9, pp. 1143-1152 (2000) (Year: 2000).*
(Continued)

*Primary Examiner* — Robert S Jones, Jr.
*Assistant Examiner* — Jiangtian Xu
(74) *Attorney, Agent, or Firm* — Hudak, Shunk & Farine Co. LPA

(57) ABSTRACT

A double network hydrogel including a polymer (A) having a persistence length between 10 and 1000 nm; a flexible polymer (B), wherein the persistence length is measured according to single molecule force microscopy measurement, wherein polymer (B) has an extended coil conformation at a first condition and a collapsed globular conformation at a second condition. Polymer (A) preferably is a polyisocyanate, while polymer (B) is a crosslinked flexible polymer like for example PNIPAM. A method for making a double network hydrogel.

18 Claims, 8 Drawing Sheets

(51) Int. Cl.
*C09D 133/26* (2006.01)
*C08J 3/24* (2006.01)
*C08F 120/54* (2006.01)

(52) U.S. Cl.
CPC ......... *C09D 133/26* (2013.01); *C08J 2333/02* (2013.01); *C08J 2333/26* (2013.01); *C08J 2477/04* (2013.01); *C12N 2533/40* (2013.01); *C12N 2533/54* (2013.01)

(58) Field of Classification Search
CPC ................ C08J 2333/02; C08J 2333/26; C08J 2477/04; C09D 133/26
See application file for complete search history.

(56) References Cited

U.S. PATENT DOCUMENTS

| | | | |
|---|---|---|---|
| 2015/0038613 A1 | 2/2015 | Sun et al. | |
| 2015/0166735 A1 | 6/2015 | Bidault et al. | |
| 2017/0342220 A1* | 11/2017 | Iijima | C08F 2/10 |

OTHER PUBLICATIONS

Zadrazil et al ("Investigation of thermo-responsive optical properties of a composite hydrogel", Colloids and Surfaces A: Physicochem. Eng. Aspects 372, 2010) (Year: 2010).*

Odian ("Principles of Polymerization", 2004) (Year: 2004).*

Almeida, et al., Temperature and pH stimuli-responsive polymers and their applications in controlled and self-regulated drug delivery, Journal of Applied Pharm Sci. 02; 2012, vol. 6, pp. 01-10, www.japsonline.com.

Boral, et al., Hierarchical structures in agar hydrogels, Polymer, 2009, vol. 50, pp. 5585-5588, Elsevier Ltd.

Chen, et al., Ultrafine Hydrogel Fibers with Dual Temperature- and pH-Responsive Swelling Behaviors, Journal of Polymer Sci, Part A,: Polymer Chemistry, 2004, vol. 42, pp. 6331-6339, Wiley Periodicals, Inc.

Dotcheva, et al., Thermosensitive networks based on high molecular weight polyoxyethylene and N-isopropylacrylamide, Polymer Bulletin, 1999, vol. 42, pp. 709-716, Springer-Verlag.

Gavrilov, et al., Stress-stiffening materials: tuning the properties, International Conference on BioNano, 2017, abstract submission.

Jaspers, et al., Nonlinear mechanics of hybrid polymer networks that mimic the complex mechanical environment of cells, Nature Communications, 2017, vol. 8, pp. 15478.

Suginome, et al., Transition Metal-Mediated Polymerization of Isocyanides, Adv. Polym. Sci., 2004, vol. 171, pp. 77-136, Springer-Verlag.

Smith, et al., March's Advanced Organic Chemistry, Reactions, Mechanisms, and Structure, Sixth Edition, 2007, pp. 1-2357, Wiley-Interscience, A John Wiley & Sons, Inc. Publication.

Zhang, et al., Single Polymer Chain Elogation of Poly(N-isopropylacrylamide) and Poly(acrylamide) by Atomic Force Microscopy, J. Phys. Chem. B, 2000, vol. 104, pp. 10258-10264, Am Chem. Soc.

Rinaudo, et al., Viscosity, On the Viscosity of Sodium Alginates in the Presence of External Salt, Polymer Bulletin 15, 1986, pp. 253-256, Springer-Verlag.

* cited by examiner

BIOMIMETIC DOUBLE NETWORK HYDROGELS

FIELD OF THE INVENTION

The invention relates to synthetic biomimetic double networks comprising polyisocyano peptide hydrogels.

BACKGROUND OF THE INVENTION

Fibrous networks of biopolymers are found in both the intracellular and extracellular matrix, where these networks determine the mechanical strength of cells and tissues. From the microscopic scale of a single cell to the macroscopic scale of fibrous tissues, biopolymers with different stiffnesses control cellular processes such as cell differentiation, proliferation, transportation and communication. In recent years, a very large number of different hydrogels has been developed, often with the goal to create an artificial extracellular matrix for biomedical applications. However, the mechanical environment inside and outside the cell is not determined by a single component. Multiple biopolymers with different structural and mechanical properties, which physically and chemically interact with each other, make the mechanical environment of a cell in vivo much more complicated than the environment of a cell in a single-component artificial matrix.

For hydrogels based on networks of synthetic flexible polymers it has been shown that the presence of a second component can dramatically change the mechanical properties of the resulting material. These so-called double-network hydrogels show extremely high mechanical strength or toughness compared to their single-component equivalents. The stiffness of such double-network gels can be much higher than simply the sum of two hydrogels composed of the individual components. In another approach, composites of macromolecules and clay or metal-oxide nanosheets were used to form hydrogels with great mechanical strength and even completely self-healing properties or anisotropic mechanics. Such outstanding mechanical properties are much more difficult to achieve in single-component hydrogels.

US 2015/038613 describes double network hydrogels of alginate and polyacrylamide. Polyacrylamide is no thermos responsive and does not show a transition from an extended coil to a collapsed globular conformation.

Dotcheva et al in Polymer Bulletin Vol 42, no 6, pages 709-716 describes hydrogels of polyoxyethylene (PEG) and PNIPAM, crosslinked with MBAA. PEG is a flexible polymer, having a persistence length smaller than 1 nm.

US 2015/166735 describes hydrogels of albumin and methacrylic modified polyvinylalcohol. The methacrylic modified polyvinylalcohol does not show a transition from an extended coil to a collapsed globular conformation.

Chen H et al in Journal of Polymer Science, Part A, vol 42, no 24, pages 6331-6339 describes hydrogels comprising PNIPAAM and polyacrylic acid. The polyacrylic acid is a flexible polymer and has a persistence length smaller than 1 nm.

WO 2015/124732 discloses a hydrogel comprising a polyisocyanopeptide and fibrin. Both the polisocyanopeptide and fibrin are semi-flexible and show a persistence length between 10 and 1000 nm. Furthermore fibrin does not show a transition from an extended coil to a collapsed globular conformation. Polyisocyanide hydrogels are known in the art. WO 2011/007012 discloses a hydrogel comprising oligo(alkylene glycol) functionalized polyisocyanopeptides. The polyisocyanopeptides are prepared by functionalizing an isocyanopeptide with oligo-(alkylene glycol) side chains and subsequently polymerizing the oligo-alkylene glycol functionalized isocyanopeptides to polyisocyanopeptides (PIC). This PIC material is a fully synthetic strain-stiffening hydrogel with an architecture of polymer bundles. A solution of these polymers in water will show Lower Critical Solution Temperature (LCST) behavior; above the LCST a hydrogel is formed by formation of a branched network of entangled semi-flexible bundles, a consequence of entropic desolvation of the ethylene glycol moieties on the polymers. In the gel phase, the material mimics mechanical properties of natural materials, including strain-stiffening in the biologically reachable regime thanks to its architecture. The semi-flexible bundles have a persistence length in the nm range, typically between 10-1000 or preferably between 100-1000 nm.

The polyisocyanide hydrogels show reversible mechanical properties as a function of the temperature, polymer concentration and for example molecular weight of the polyisocyanopeptide. In some applications different mechanical properties are desired as can be achieved by the polymeric hydrogel. There is a need for additional methods to tune the mechanical properties of PIC hydrogels, including methods that in-situ, i.e. with external stimuli only, reversibly manipulated the mechanics.

SUMMARY OF THE INVENTION

It is an object of the present invention to provide a tunable hydrogel system, having for example high stiffness values at low temperatures.

The invention relates to a double network hydrogel comprising a. A polymer (A) having a persistence length between 10 and 1000 nm b. A flexible polymer (B) having a persistence length smaller than 1 nm, wherein the persistence length is measured at room temperature in an aqueous solution at neutral pH according to single molecule force microscopy measurement, and wherein polymer (B) has an extended coil conformation at a first condition and a collapsed globular conformation at a second condition.

In an embodiment of the invention the flexible polymer (B) is temperature responsive (thermoresponsive) polymer having a lower critical solution temperature (LCSTb), whereby the condition 1 is present at a temperature below LCSTb and condition 2 is present at a temperature above the LCSTb.

In another embodiment of the invention the flexible polymer (B) is a pH responsive polymer. For a pH-responsive polymer (B), condition 1 could be above the polymer pKa and condition 2 could be above it, or vice versa.

DETAILED DESCRIPTION OF THE INVENTION

Figure 1:
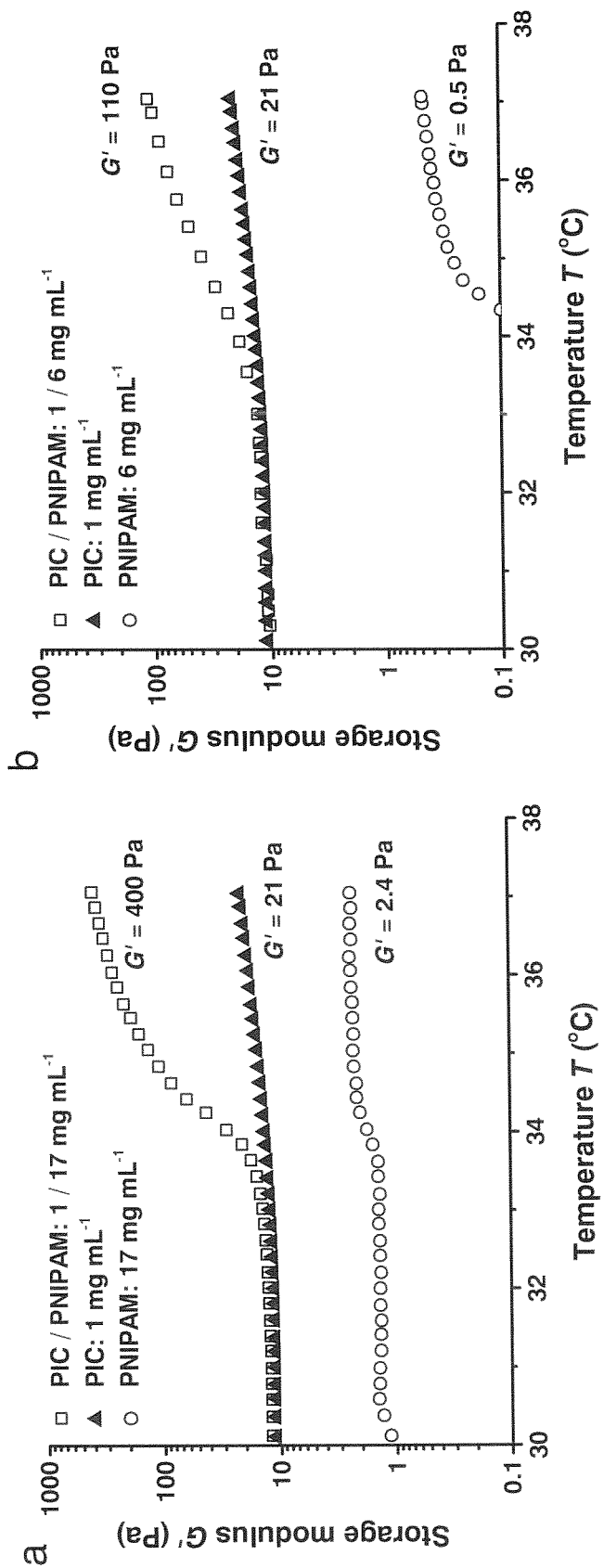
FIG. 1 shows thermoresponsive mechanical properties of PIC-PNIPAM double-network hydrogels. (a) Double-network gels with 1 mg mL-1 PIC and 17 mg mL-1 NIPAM show a very large increase in stiffness at the LCST of NIPAM compared to the single-network hydrogels at the same polymer concentrations. (b) For double-network gels with 1 mg mL-1 PIC and 6 mg mL-1 NIPAM, the increase in G' with temperature is smaller but still significantly larger than for both single-component hydrogels.

Polymer (A) is a semi-flexible polymer having a persistence length between 10 and 1000 nm. The persistence length is the length of a straight segment of a polymer chain or bundle of polymer chains. It can be measured by single molecule force microscopy measurements at room temperature in an aqueous environment at neutral pH (pH=7).

In a network of semi-flexible chains or bundles, the pore size is of the same order of magnitude as the persistence length of the chains or bundles.

Preferably the persistence length of the bundles ranges between 100 and 1000 nm, more preferably between 250 and 900 nm.

Examples of polymers A are polyisocyanopeptides, DNA, actin, fibrin, intermediate filaments, collagen and cellulose derivatives.

Preferred examples of polymer (A) are polyisocyanopeptides. More preferably the polyisocyanopeptides are oligo (alkylene glycol)functionalized poly(isocyanopeptide)s such as disclosed in WO2011007012 (which is herein incorporated by reference).

Such polymers can be prepared by the polymerization of oligo(alkylene glycol) functionalized isocyanopeptides.

The monomers are preferably based on a di-, tri-, tetra- or more peptidic motif substituted at the C terminal with the desired oligo(alkylene glycol) chains. The chains may be based on linear, branched or dendronized oligo(alkylene oxide). Preferably the chain is linear and is composed of ethylene glycol units.

The peptidic segment can be of different compositions determined by the sequence of natural or non natural and expanded amino acids or mixture thereof.

The monomers are derived from adequate oligo(alkylene glycol) fragments. A multi-steps peptidic coupling strategy is used to introduce successively the desired amino-acids. Following the introduction of the desired peptidic sequence, the N-terminus of the peptidic segment is formylated with an adequate formylation method. This formylation may include the treatment of the product with formyl salts, formic acid, or other formylating agents.

Some examples of formylation strategies make use of formate salts (such as sodium or potassium formate), alkyl formates (such as methyl-, ethyl-, or propyl-formate), formic acid, chloral and derivatives. The isocyanide is then formed by treating the formamide with an appropriate dehydration agent. An example of dehydratation strategy uses diphogene. Several examples of dehydratation agents that may also be used are phosgene and derivatives (di-, triphosgene), carbodiimides, tosyl chloride, phosphorous oxachloride, triphenylphosphine/tetrachlorocarbon, [M. B. Smith and J. March "March's advanced organic chemistry" 5th edition, Wiley & Son eds., 2001, New York, USA, pp1350-1351 and ref. herein;]

Examples of suitable alkylene glycols are ethylene-, propylene-, butylene- or pentylene glycol. Preferably the alkylene glycol is ethylene glycol.

Advantageous oligoethyleneglycol units are depicted below. In general, the term oligo refers to a number<10.

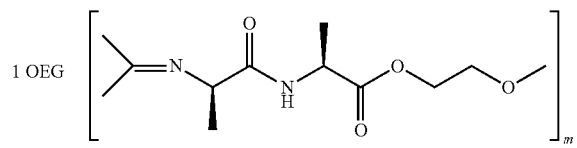

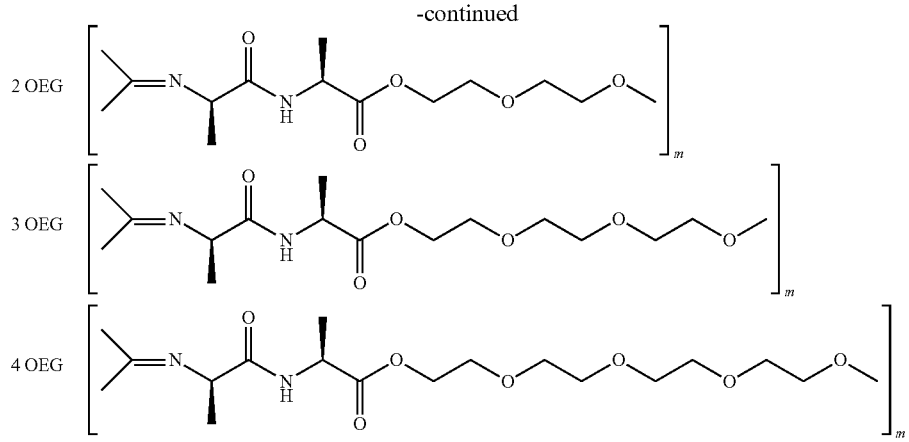

Preferably the isocyanopeptides are functionalized with at least 3 ethylene glycol units to lead to water soluble materials after polymerization.

The polysiocyanopeptides can be grafted with a linking group to further attach functional moieties to the polymer chain. WO2015007771 discloses copolymers that contain functional groups like for example cell adhesion factor and the like. WO2015007771 is hereby incorporated by reference.

(Co)polymerization can be performed in the presence of an apolar solvent. Suitable apolar solvents may be selected from the group consisting of saturated hydrocarbon solvents and aromatic hydrocarbon solvents or mixtures thereof. Examples of apolar solvents are pentane, hexane, heptane, 2-methylbutane, 2-methylhexane, cyclohexane, and toluene, benzene, xylenes or mixtures thereof. Preferably toluene is used in the polymerization. Preferably toluene is chosen for the polymerization process of oligo(ethylene glycol) isocyanopeptides where the oligo(ethylene glycol) part contains at least three ethylene glycol units.

Preferably the polymerization is carried out in the presence of a catalyst. The catalyst is preferably a nickel(II) salt. Example of Ni(II) salts are nickel(II) halides (e.g. nickel(II) chloride), nickel(II) perchlorate or tetrakis-(tertbutylisocyanide)nickel(II) perchlorate.

Other complexes and nickel salts might be used provided that they are soluble in the polymerization medium or initially dissolved in an adequate solvent which is miscible in the polymerization medium. General references describing some catalytic systems that may be used to polymerize the oligo(alkylene glycol)isocyanopeptides may be found in Suginome M.; Ito Y; Adv Polym SC1 2004, 171, 77-136; Nolte R. J. M.; Chem. Soc. Rev. 1994, 23(1), 11-19)].

Preferably the monomer concentration is chosen above 30 mmol/L and the catalyst/monomer ratio chosen between 1/100 and 1/10 000. Low nickel(II) concentrations will result in high molecular weight polymer hydrogelators, whereas high nickel(II) concentrations will yield shorter PIC polymers.

In a representative example, a millimolar solution of monomer in a nonpolar organic solvent or mixture of solvents is added to a nickel (II) catalyst dissolved in a polar solvent in a molar ratio of 1:50 up to 1:100,000 catalyst to monomer. In a sealed environment the mixture is vigorously stirred for 2 to 24 hrs. Once completed, the reaction mixture is evaporated and the crude product is dissolved in organic solvents and precipitated in diethylether or similar non-compatible organic solvents, giving the desired product.

Polyisocyanopeptides (PIC) that are suitable as polymer (A) in the hydrogel according to the present invention have a LCSTa between 5 and 50° C., preferably between 15 and 35° C.

The PIC polymers give a hydrogel at very low concentrations, typically between 0.25 mg/ml and 3.0 mg/ml above the LCSTa. Below the LCSTa the polymer does not form a hydrogel.

The viscosity average molecular weight of polymer (A) typically ranges between 200 and 1000 kg/mol (kDalton), preferably between 250 and 700 kg/mol. The viscosity average molecular weight $M_v$ is determined from the polymer's intrinsic viscosity $[\eta]$, as measured in dilute (0.01-0.06 mg/mL) acetonitril solutions at 25° C., using the Mark-Houwink equation: $[\eta]=K\ (M_v)^a$ with the Mark-Houwink parameters $K=1.4\times10^{-9}$ and $a=1.75$, which were used before for polyisocyanides.

The double network contains a responsive flexible polymer (B).

The responsive flexible polymer (B) can be responsive to different stimuli. For example, the polymer can be thermoresponsive (temperature responsive). Alternatively the polymer (B) can be for example pH-responsive. In all cases the polymer (B) will change from an extended coil conformation at a first condition and a collapsed globular conformation at a second condition, and wherein the transition between the first and second condition is marked by a certain temperature, or pH.

Polymer (B) is a flexible polymer, having a persistence length in the sub-nanometer range (this is smaller than 1 nm).

Polymer (B) is preferably either physically or chemically crosslinked. In case polymer (B) is thermoresponsive, usually the extended coil conformation occurs below the LCSTb, while contraction of the flexible polymer (B) takes place at the LCSTb and a contracted polymer (B) can be found above the LCSTb. The extended coil conformation is shown as a swollen or expanded structure below the LCST of polymer (B) (LCSTb). The transition from swollen hydrogel to contracted hydrogel is reversible. A swollen hydrogel has a larger volume compared to a contracted hydrogel, which means that the polymer concentration (g/ml) of the hydrogel below the LCSTb is lower than the polymer concentration (g/ml) of the hydrogel above the LCSTb.

Preferably the LCSTb is higher than the LCSTa, preferably at least 2° C. higher, compared to the LCSTa. In a preferred embodiment the LCSTb ranges between 20 and 40° C., and is at least 2° C. higher than the LCSTa, preferably at least 4° C. higher than the LCSTa.

Examples of suitable thermally-responsive networks are polymers composed of N-isopropylacrylamide, N,N-diethylacrylamide, N-ethylacrylamide, N-propylacrylamide their copolymers and their copolymers with other acrylic or acrylamide monomers, including acrylic acid, methyl acrylate, ethyl acrylate, butyl acrylate, hydroxyethyl acrylate, hydroxypropyl acrylate, acrylamide and N,N-dimethyl acrylamide, as well as the methacrylate equivalents. To form a network, a small amount of a crosslinker, such as N,N'-methylenebisacrylamide (MBAA), or another di-, tri-, or multifunctional acrylate or methacrylate is added in the polymerization stage.

Preferably polymer (B) is selected from poly(N-isopropylamide) (PNIPAM) or poly(N,N-diethyl acrylamide) (PDEAM).

In a preferred embodiment, polymer (B) is poly(N-isopropylacrylamide) (PNIPAM), which is a flexible polymer that, similar to PIC (preferred polymer (A)), shows LCST behavior. Heating a solution of PNIPAM polymers beyond their LCST of 32° C. changes the conformation of the polymers from an extended coil to a globular structure. In other words, hydrogels based on a crosslinked PNIPAM show extensive shrinking when heated beyond the LCST and high degrees of swelling when cooled below the LCST.

The polymers can be crosslinked through copolymerization with for example N,N'-methylenebisacrylamide (MBAA), resulting in a chemically crosslinked network of flexible polymers, which is thermoresponsive.

In case polymer (B) is pH responsive, a change in chain conformation (from extended to collapsed coil) occurs at the pKa of the polymer. Dependent on the polymer used, the collapsed conformation can occur above or below the pKa and consequently, the (reversible) transition from a swollen to a collapsed hydrogel can be accomplished by either raising or lowering the pH of the solution.

Examples of suitable pH-responsive networks are polymers composed of monomers 1-37 or copolymers thereof, that are crosslinked with a small amount of a crosslinker, such as N,N'-methylenebisacrylamide (MBAA), or another di-, tri-, or multifunctional acrylate or methacrylate that is added in the polymerization stage.

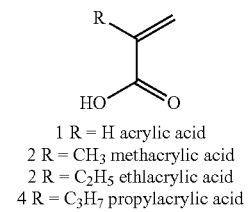

1 R = H acrylic acid
2 R = CH₃ methacrylic acid
2 R = C₂H₅ ethlacrylic acid
4 R = C₃H₇ propylacrylic acid

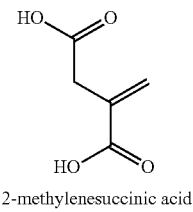

5 2-methylenesuccinic acid

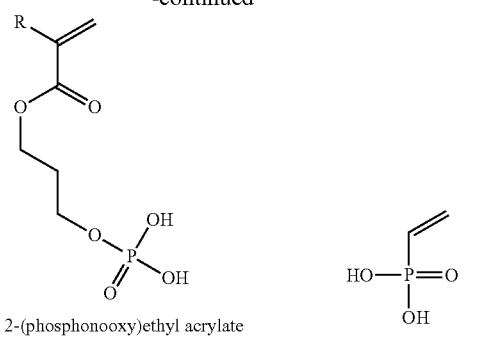

6 R= H 2-(phosphonooxy)ethyl acrylate
7 R= CH₃ 2-(phosphonooxy)ethyl methacrylate
8 vinylphosphonic acid

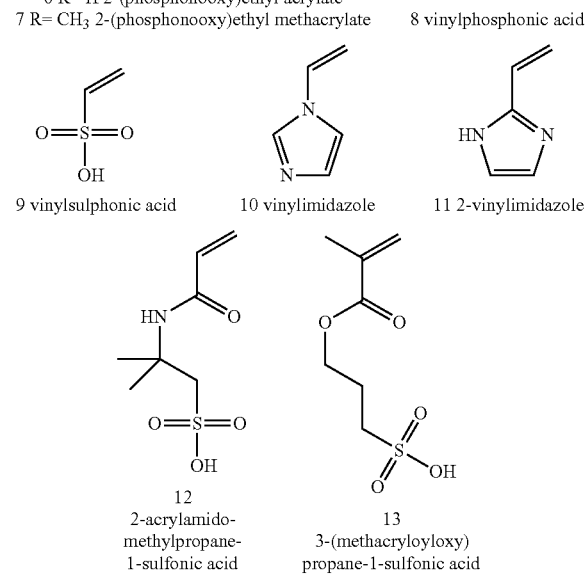

9 vinylsulphonic acid
10 vinylimidazole
11 2-vinylimidazole 12
2-acrylamido-methylpropane-1-sulfonic acid 13
3-(methacryloyloxy)propane-1-sulfonic acid

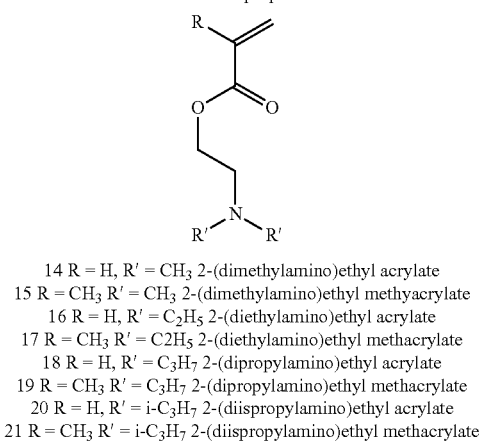

14 R = H, R' = CH₃ 2-(dimethylamino)ethyl acrylate
15 R = CH₃ R' = CH₃ 2-(dimethylamino)ethyl methyacrylate
16 R = H, R' = C₂H₅ 2-(diethylamino)ethyl acrylate
17 R = CH₃ R' = C2H₅ 2-(diethylamino)ethyl methacrylate
18 R = H, R' = C₃H₇ 2-(dipropylamino)ethyl acrylate
19 R = CH₃ R' = C₃H₇ 2-(dipropylamino)ethyl methacrylate
20 R = H, R' = i-C₃H₇ 2-(diispropylamino)ethyl acrylate
21 R = CH₃ R' = i-C₃H₇ 2-(diispropylamino)ethyl methacrylate

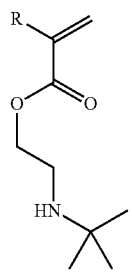

22 R = H 2-(tert-butylamino)-ethyl acrylate
23 R = CH₃ (tert-butylamino)-ethyl methacrylate

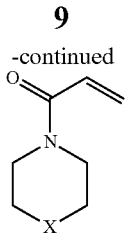

24 X = O N-acryloylmorpholine
25 X = NCH₃ N-acryloyl-N'-methylpiperazine
26 X = NC₂H₅ N-acryloyl-N'-ethylpiperazine
27 X = NC₃H₇ N-acryloyl-N'-propylpiperazine

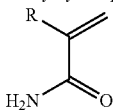

28 R = H acrylamide
29 R = CH₃ methacrylamide

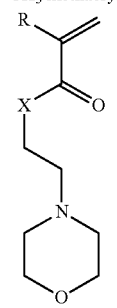

30 X = O, R = H 2-(N-morpholino)ethyl acrylate
31 X = O, R = CH₃ 2-(N-morpholino)ethyl methyacrylate
32 X = NH, R = H 2-(N-morpholino)ethyl acrylamide
33 X = NH, R = CH₃ 2-(N-morpholino)ethyl methacrylamide

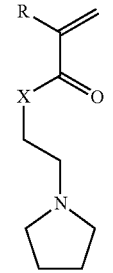

30 X = O, R = H 2-(N-pyrrolidinyl)ethyl acrylate
31 X = O, R = CH₃ 2-(N-pyrrolidinyl)ethyl methyacrylate
32 X = NH, R = H 2-(N-pyrrolidinyl)ethyl acrylamide
33 X = NH, R = CH₃ 2-(N-pyrrolidinyl)ethyl methacrylamide (Monomers for pH-responsive polymer (B) networks.)

In an embodiment polymer (B) is preferably selected from poly(acrylic acid) (PAAc) or poly(2-(dimethylamino)ethyl-ethyl acrylate) (PDMA), copolymerized with acrylamide, most preferably polymer (B) is PAAc with acrylamide. Preferably, the crosslinker used is MBAA.

Analogously, when polymer (B) is poly(acrylic acid) (PAAc), it will be a flexible polymer that shows a conformational change from an extended coil to a globule when lowering the pH of the solution. The polymers can be crosslinked through copolymerization with N,N'-methylenebisacrylamide (MBAA), resulting in a chemically crosslinked network of flexible polymers, which is pH-responsive.

Hydrogels based on a crosslinked PAAc network show extensive shrinking when heated at low pH and high degrees of swelling at high pH.

The combination of a double network hydrogel comprising a semi flexible polymer (A) and a flexible thermo- or pH-responsive polymer (B) generates a strain stiffening double-network hydrogel with both high mechanical strength and responsive mechanical properties.

A double-network hydrogels is formed, by polymerizing a PNIPAM network below its LCST in the presence of a pre-formed PIC network.

Heating this hybrid gel, or lowering the pH of the solution is expected to change the structure of the network of polymer (B), but extensive shrinking is now prevented by the interpenetrating PIC network. The structural changes of the polymer (B) network can now trigger a stiffening response, by locally deforming the PIC network. In this way, the thermal or pH cue is now transformed into a stress-induced stiffening response.

The extent of the stiffening induced by polymer (B) will be determined by the concentration of the network of polymer (B) in the sample. High concentrations of polymer (B) will give rise to a stronger effect, i.e. a stiffer polymer (A) network, lower concentrations of polymer (B) will give rise to a less strong effect, i.e. a less strongly stiffened polymer (A) network. When the concentration of polymer (B) is too low (below 1 mg/mL), the stiffening effect is very small; when the concentration of polymer (B) is too high (above 100 mg/mL), its mechanical properties will dominate those of polymer (A) and the stiffening effect cannot be observed. Typical concentrations of polymer (B) are between 1 and 100 mg/mL, preferably between 3 and 30 mg/mL.

A typical concentration of the crosslinker (preferably MBAA) is between 0.1 and 5 mol-% of the monomer concentration of polymer (B), preferably between 0.25 and 3 mol-%, more preferably between 0.5 and 2 mol-%.

The invention also relates to a process for making the double-network hydrogel according to the present invention. The process for making the double network hydrogel comprises the steps of a. Provide an aqueous solution of polymer (A) at a temperature below the lower critical solution temperature of polymer (A) (LCSTa);
b. Provide monomers B to be polymerized to polymer (B) having a LCSTb
c. Mix the aqueous solution of polymer (A) with monomers (B) and subsequently heat the mixture to a temperature above the LCSTa and below the LCSTb to provide a hydrogel comprising polymer (A) and monomers (B);
d. Induce polymerization of monomers (B) at a temperature above LCSTa and below LCSTb to provide a double network hydrogel;

wherein polymer (A) is a polymer as defined above and wherein polymer (B) is a polymer as defined above.

The polymerization in step d is preferably carried out between 15 and 50° C. In the case of a thermoresponsive polymer, the polymerization step is carried out above LCSTa and below LCSTb. Polymerization can be carried out with the addition of polymerization initiators like for example potassium, sodium or ammonium persulfate with or without tetramethylethylenediamine (TEMED) or like hydrogen peroxide and a suitable reductor, such as $Fe^{2+}$. Alternatively, the polymerization reaction is initiated photochemically with for instance Irgacure 2959 and irradiated by UV light. The concentration initiator is for example 10 mM.

The polymerization is carried out in water or aqueous solutions.

The invention also relates to the use of the hydrogel, for example for culturing cells.

The invention further relates to coatings comprising the oligoalkylene functionalized polyisocyano-peptide according to the present invention. The invention may further be used to prepare optically active material for chiral separation in water, injectable biocompatible thermogelling agent for tissue engineering (non functionalized polymers or functionalized with peptides for cell adhesion, stimulation, biocompatible synthetic extracellular matrix mimic/matrix for neurone regeneration (biologically active aligned fibers).

The hydrogels provided herein may advantageously be used for the bioactive coating of materials] films, membranes), for the stabilization of biomolecules and cells in organic and aqueous media for catalysis. These hydrogels may be prepared by covalent linking of the biomolecules or cells, by—physical trapping of biomolecules or cells.

EXAMPLES

N-isopropylacrylamide (NIPAM) has to be polymerized at lower temperature, below the LCST of PNIPAM. The NIPAM polymerization was performed at T=30° C. and was initiated by the addition of potassium persulfate and tetramethylethylenediamine (TEMED), the latter accelerates the rate of formation of free radicals from persulfate at this lower temperature. To form a PIC-PNIPAM double-network hydrogel, a cold solution of PIC was mixed with a solution of NIPAM and MBAA, keeping the monomer to crosslinker ratio constant at 0.5 mol %, after which potassium persulfate and TEMED were added to initiate the formation of the chemically crosslinked PNIPAM network. This mixture was transferred to the rheometer (TA Instruments, Discovery HR-2, aluminium parallel plate geometry with a plate diameter of 40 mm and a gap of 500 µm) and heated to T=30° C. instantly, and PIC-PNIPAM double-network hydrogels were obtained after incubation at T=30° C. for at least 1 hour between the rheometer plates.

After formation of both polymer networks, the thermoresponsive mechanical properties of the PIC-PNIPAM hybrid hydrogels were measured by heating the samples to T=37° C., beyond the LCST of the PNIPAM network. FIG. 1 shows G' as function of temperature for the double-network hydrogels at two different PNIPAM concentrations (17 and 6 mg mL-1 or 0.15 and 0.05 M) compared to G' of both single-network hydrogels upon heating. Single-component hydrogels of either PIC or PNIPAM show only a small increase in stiffness with temperature, resulting in very soft gels at T=37° C. at these low polymer concentrations, At the lowest NIPAM concentration of 6 mg mL-1, the sample without PIC (pink dots) does not form a hydrogel but remains liquid with G' close to zero, whereas at 17 mg mL-1, PNIPAM forms a very weak hydrogel with a modulus of only 2 Pa. The PIC-PNIPAM double-network gels, however show a much larger increase in G' upon heating beyond the LCST of the PNIPAM network (T≈33° C.), resulting in much stiffer gels at T=37° C. For the PIC-PNIPAM hydrogel with 17 mg mL-1 NIPAM (FIG. 1a), G' is about 20 times higher than the moduli of the individual components added up. This 20-fold increase in stiffness occurs within just a few degrees Celsius. For the double-network hydrogel with a lower NIPAM concentration of 6 mg mL-1 (FIG. 1b), the increase in G' with temperature is smaller but the final stiffness is still about 5 times higher compared to the single-network hydrogels. So the double-network gels even show a thermal response at very low NIPAM concentrations, at which the PNIPAM network by itself is too weak to form a hydrogel at all.

The strong thermal stiffening response of the double-network hydrogels originates from the strain stiffening of the PIC network. Upon heating the gels, the PNIPAM network contracts at its LCST and, thereby, deforms the interpenetrating PIC network. This internal deformation of the PIC network stretches the semi-flexible bundles, resulting in a strain stiffening response of the double-network hydrogel. The observed increase in stiffness of about 1 to 2 orders of magnitude at the LCST is similar to the increase in stiffness when an external stress is applied to a PIC hydrogel. The smaller increase in G' for a lower NIPAM concentration indicates that a less dense PNIPAM network applies a smaller internal stress to the interpenetrating PIC network at its LCST. A similar strain stiffening response triggered by an internal stress has been observed for composite networks of actin filaments and myosin motors. In these hydrogels, the molecular motors also internally stiffen the network, by pulling on the semi-flexible actin filaments, resulting in an increase in stiffness up to two orders of magnitude.

Figure 2:
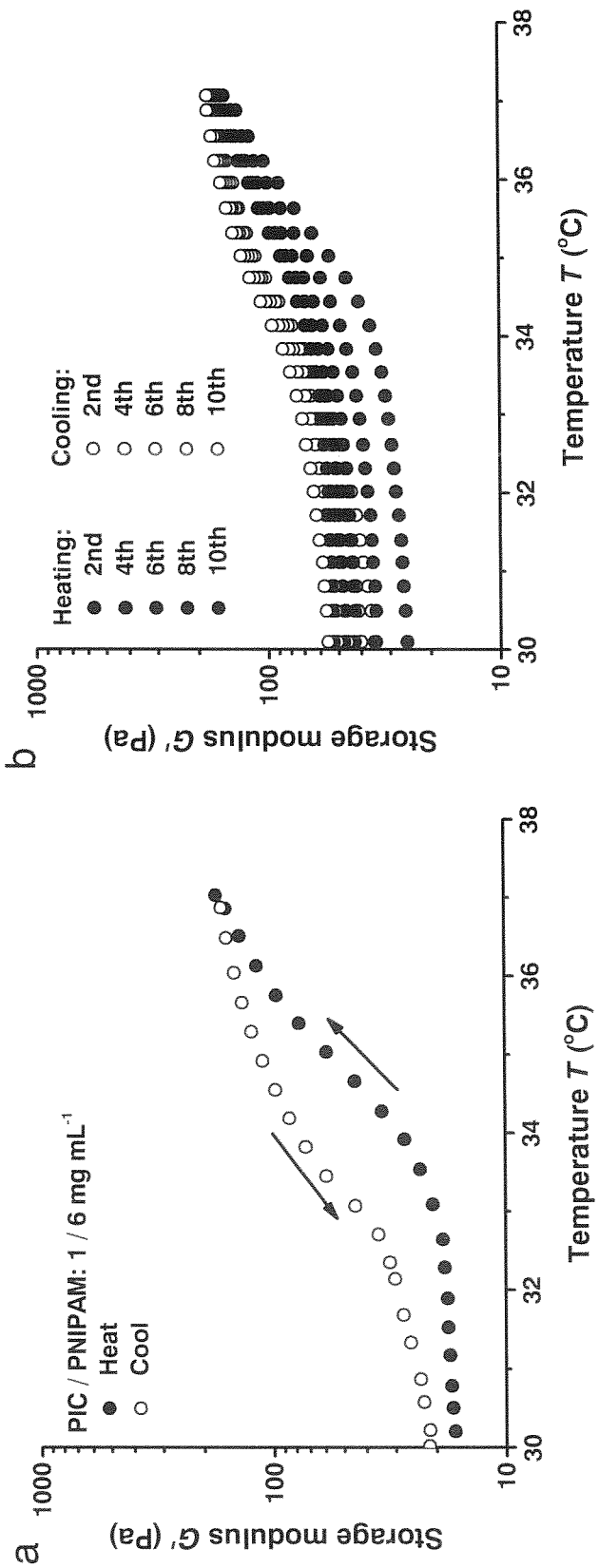
FIG. 2 shows reversible stiffening and softening of PIC-PNIPAM double-network hydrogels. (a) Storage modulus as a function of temperature for a double-network hydrogel with 1 mg mL-1 PIC and 6 mg mL-1 NIPAM upon heating and cooling between T=30 and 37° C. (b) Multiple heating and cooling cycles for the same PIC-PNIPAM double-network gel, showing a small increase G' after every cycle.

Since both the thermal response of the PNIPAM network and the strain stiffening response of the PIC network are reversible, one may expect that the thermal stiffening response of the double-network hydrogels is also fully reversible. To test this hypothesis, a sample with 1 mg mL-1 PIC and 6 mg mL-1 of NIPAM was heated and cooled between T=30 and 37° C. at a rate of 1° C. min-1 (FIG. 2a). Although some hysteresis is observed upon cooling down, G' decreases to a value that is close to the stiffness of the double-network hydrogel before heating. This reversibility is very similar to the reversible response of strain stiffening hydrogels to an externally applied shear stress. This heating and cooling cycle can be repeated multiple times on the same sample, as shown in FIG. 2b. The double-network hydrogel shows the same stiffening response upon heating beyond the LCST of PNIPAM, even after 10 cycles. Upon cooling however, G' does not fully decrease to its original value which results in a slightly higher gel modulus at T=30° C. after every cycle.

The higher gel stiffness after every temperature cycle indicates that the PIC network does not fully relax after cooling down below the LCST of the PNIPAM network. A fraction of the PIC fibers probably remain stretched after swelling of the PNIPAM network, which leads to a slightly higher G' after each heating and cooling cycle. An alternative explanation could be that the shrinking and swelling of the PNIPAM network causes a structural change in the PIC network, such as extra entanglements between the PIC bundles which would lead to a higher crosslink density of the bundled network.

Figure 3:
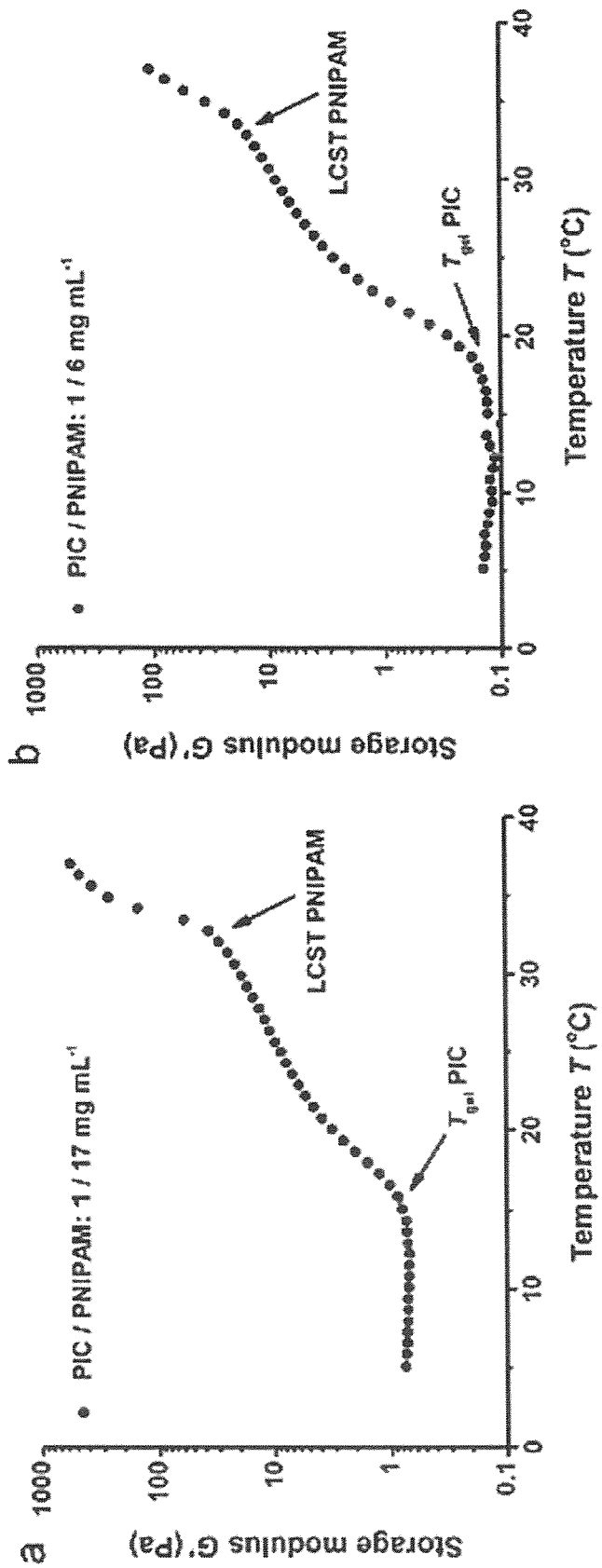
FIG. 3 shows double thermal transitions of PIC-PNIPAM double-network hydrogels with 1 mg mL-1 PIC and (a) 17 mg mL-1 NIPAM or (b) 6 mg mL-1 NIPAM. Both at the gelation temperature of the PICs and at the LCST of PNIPAM, the double-network hydrogel modulus increases by more than an order of magnitude. The heating rate is 1.0° C. min-1 for both samples.

Because both PIC and PNIPAM are thermoresponsive polymers, their double-network hydrogels are expected to show two thermal transitions. The PIC-PNIPAM gels are formed at T=30° C., which is in between the gelation temperature Tgel of PIC and the LCST of PNIPAM. Therefore, the temperature was first lowered to T=5° C., which leads to solvation of the PIC polymers. The modulus at T=5° C. represents the stiffness of only the PNIPAM network. PIC-PNIPAM double-network samples with 17 or 6 mg mL-1 NIPAM were subsequently heated to T=37° C. to trigger the thermal response of both polymers (FIG. 3). Indeed, two thermal transitions are observed which both lead to a large increase in G' of the composite hydrogel. Heating beyond Tgel of PIC increases the hydrogel modulus by more than an order of magnitude due to the formation of the PIC network and further heating, beyond the LCST of PNIPAM, again strongly increases G' as a result of strain stiffening response the PIC network. The sample with the lower NIPAM concentration is liquid at low temperatures with G' close to 0 Pa (FIG. 3b), but upon heating also two thermal transitions are observed. The modulus of both gels increases by about a factor 1000 within a small temperature range of only ~30° C. This highlights that the PIC-PNIPAM double-network hydrogels are extremely responsive to temperature and that their stiffness can be controlled over a broad range, even at the very low polymer concentrations used in the examples discussed here.

Figure 4:
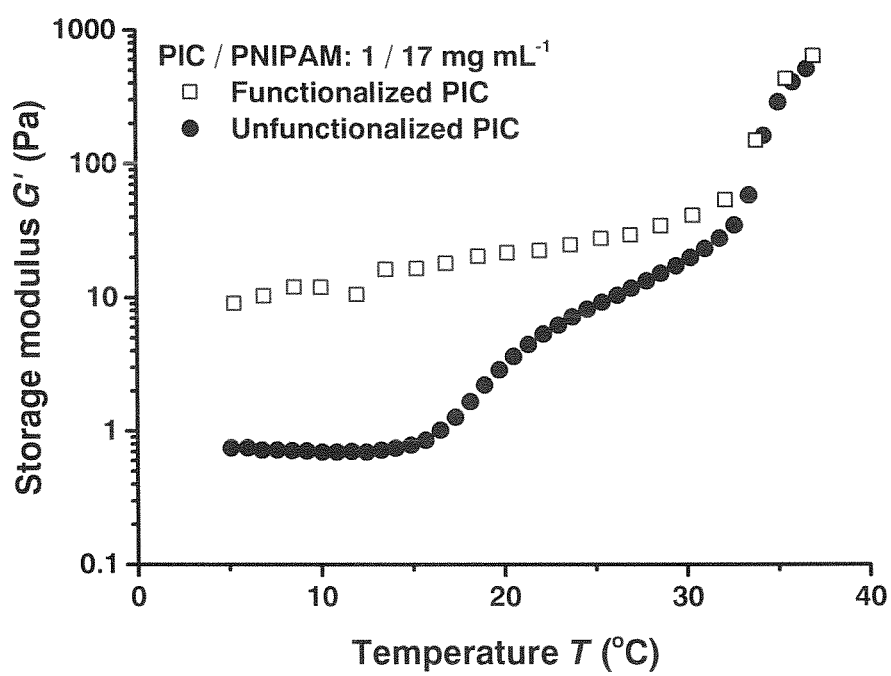
FIG. 4 shows thermoresponsive mechanical properties of PIC-PNIPAM double-network hydrogels with conjugated polymer networks (red squares) or interpenetrating polymer networks (black dots). The heating rate is 1° C. min-1 for both samples.
Figure 5:
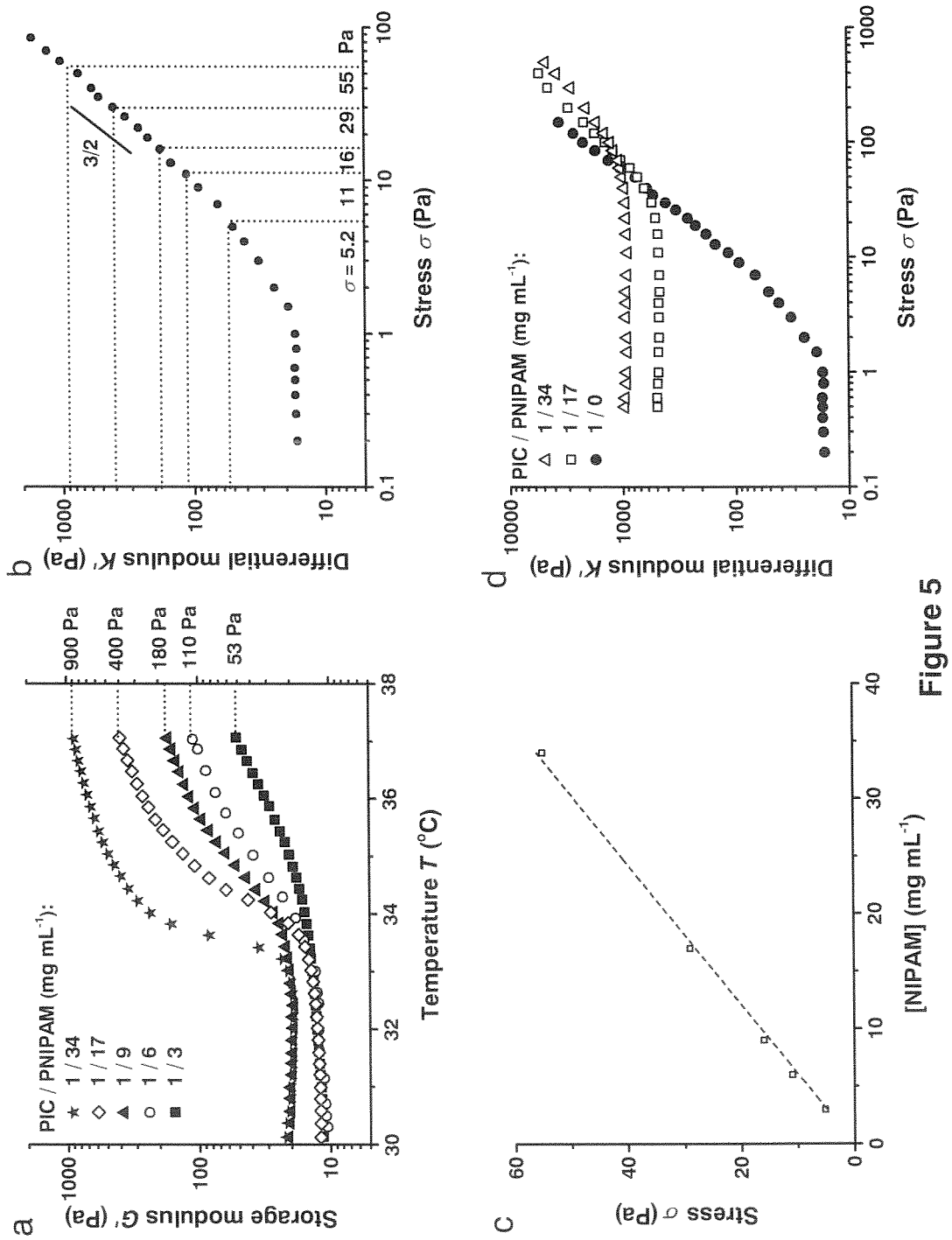
FIG. 5 shows strain stiffening of PIC in response to internally and externally applied stress. (a) Increasing the NIPAM concentration of PIC-PNIPAM double-network hydrogels increases the magnitude of the thermally induced stiffening response of the composite gel. (b) Differential modulus K' as a function of external pre-stress σ for a 1 mg mL-1 PIC hydrogel at T=33° C. The dotted lines correspond to the modulus of the PIC-PNIPAM double-network gels at T=37° C. and the pre-stress σ required to reach this stiffness for the PIC hydrogel. (c) The internal stress generated by the PNIPAM network upon heating increases linearly with NIPAM concentration. (d) K' as a function of external pre-stress a for PIC-PNIPAM hydrogels at T=37° C., The internal stress generated by the NIPAM network not only increases the linear modulus but also the critical stress of the composite hydrogels.

By using acrylamide-functionalized PICs, we can also form double-network hydrogels with conjugated PIC and PNIPAM networks. The functionalized PIC polymers were again mixed with NIPAM, MBAA, potassium persulfate and TEMED and subsequently incubated at T=30° C. for at least 1 hour between the rheometer plates. We tested the thermoresponsive properties of these hydrogels in the range of T=5 to 37° C. (FIG. 4). When heated from T=30 to 37° C., the gels with covalently linked polymer networks show exactly the same stiffening response as PIC-PNIPAM hydrogels with unfunctionalized PICs. This indicates that both the thermal response of the PNIPAM network and the strain stiffening response of the PIC network are not affected by the covalent interactions between the two networks. At T=30° C. the modulus of the composite hydrogel with functionalized PICs is slightly higher than for the unfunctionalized PICs, which is caused by an increased crosslink density of the composite network similar to the PIC-PAAM double-network gels.

At lower temperatures below T=30° C., however, the response of the covalently linked networks is very different from the interpenetrating PIC-PNIPAM network. When cooled to T=5° C., the modulus of the composite gel with functionalized PICs only decreases by about a factor two and upon reheating, the first thermal transition at the gelation temperature of the PICs is not observed any longer (FIG. 4). This means that the PIC network does not dissolve at low temperatures when it is covalently linked to a second polymer network. The PIC chains within a polymer (B)undle are probably linked to each other by short PNIPAM chains and do not only interact through reversible hydrophobic interactions. Consequently, the polymer (B)undles and thereby the network cannot disassemble when the hydrophobicity of the polymers is decreased by cooling below Tgel. The decreasing hydrophobicity of the PICs does lead to a small decrease in G' at lower temperatures. So by crosslinking the PICs with a second polymer network, the bundled network remains intact at low temperatures, but we keep the thermoresponsive behaviour at high temperature.

Figure 6:
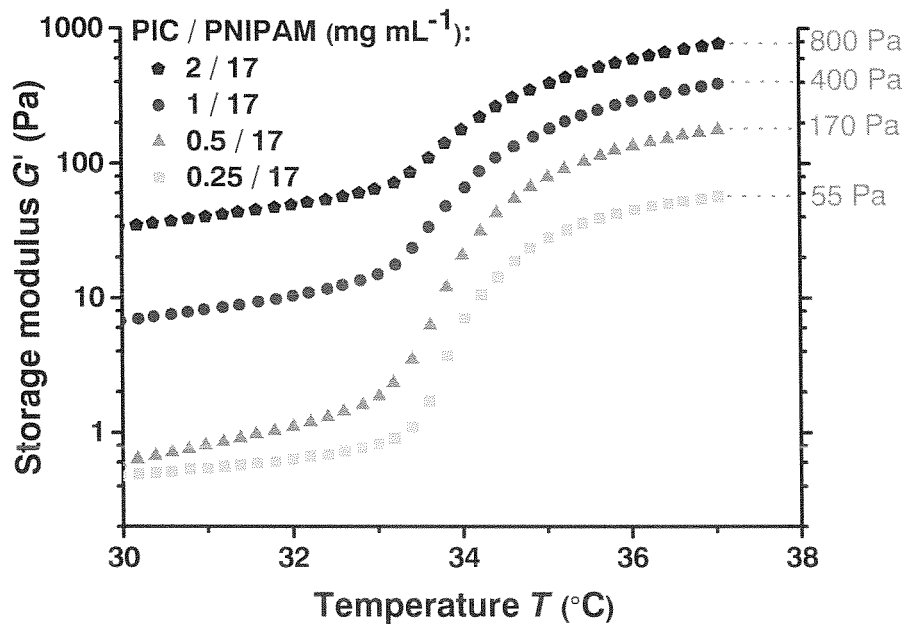
FIG. 6 shows effect of PIC concentration on rheological properties of the hybrid hydrogel.

Example: PIC-PNIPAM hybrids were prepared in deionised water with PIC concentrations of 0.25-2 mg/mL and a constant PNIPAM concentration 17 mg/mL. The samples were prepared by mixing the NIPAM monomer, crosslinker (0.5%) and initiator system, and heating the solution to 30° C. until the polymerisation is finished. All hybrids display a step in the storage modulus at the transition temperature of PNIPAM (LCSTb≈33° C.). The effect of the PIC concentration on rheological properties of the hybrid hydrogel is shown in FIG. 6.

Figure 7:
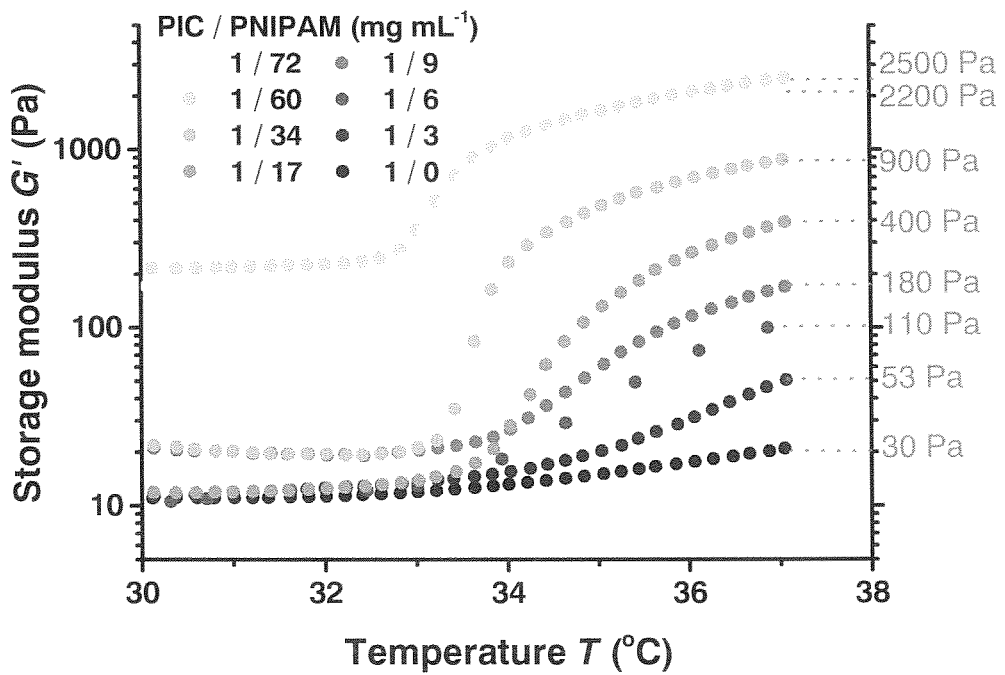
FIG. 7 shows effect of PNIPAM concentration of the mechanical properties of the hybrid hydrogels. Above 60 mg mL-1 the modulus is dominated by PNIPAM network.
Figure 8:
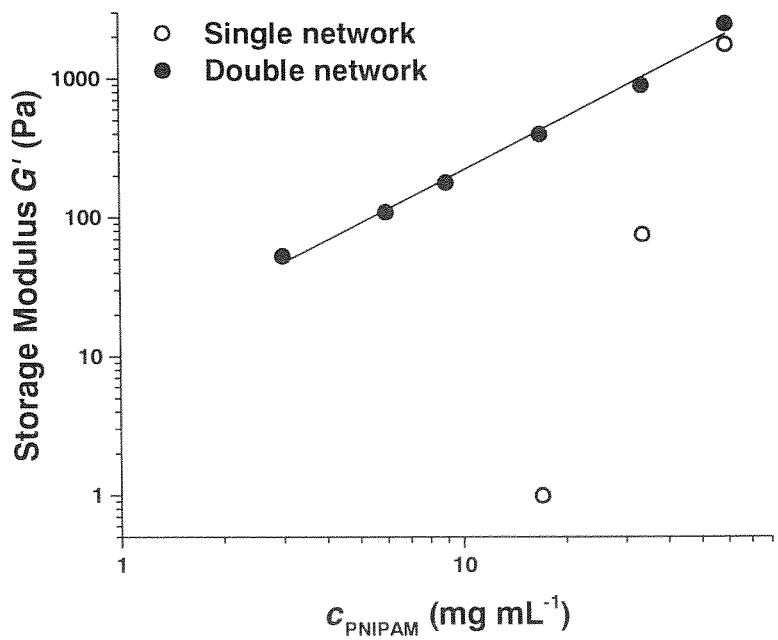
FIG. 8 shows variation of the storage modulus (G') with PNIPAM concentration for the double network PIC and PNIPAM and single network (PNIPAM) at fixed temperature of 37° C. G' of the double and single networks are close when c_PNIPAM>60 mg mL-1, and therefore the stiffening effect from the PIC network is negligible.

Example: PIC-PNIPAM hybrids were prepared in deionised water with a constant PIC concentration of 1 mg/mL and PNIPAM concentrations 3-72 mg/mL (FIG. 7), following the procedure described above. All hybrids display a step in the storage modulus at the transition temperature of PNIPAM (LCSTb≈33° C.). At a PNIPAM concentration >60 mg/mL, the storage modulus increase becomes dominated by the stiffening of PNIPAM and PIC contributes very little (see also FIG. 8).

Figure 9:
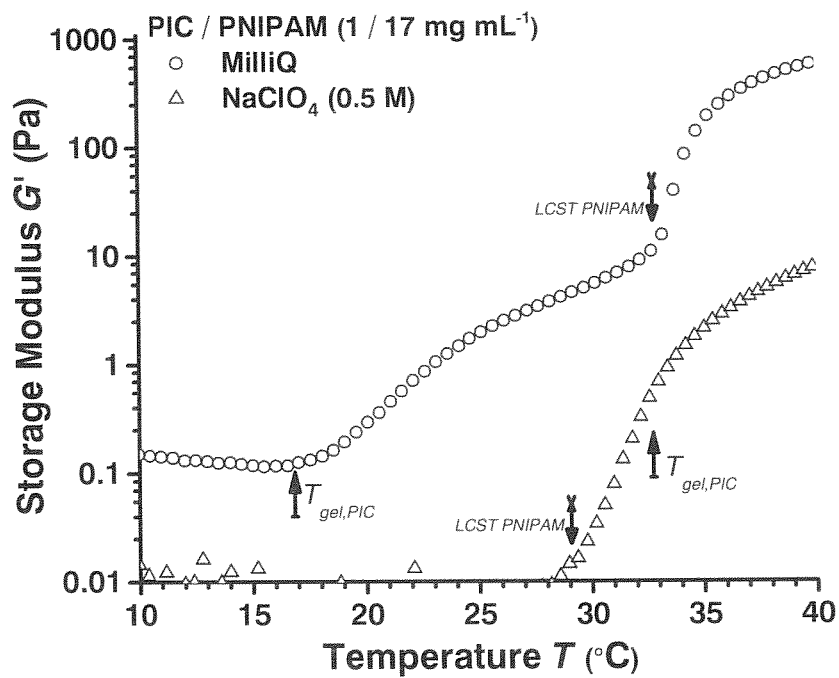
FIG. 9 shows rheological mechanical properties of the hybrid hydrogel in MilliQ water and in NaClO4 solution. In the salt solution, the LCSTPNIPAM<LCSTPIC, which prevents the PIC network to be stressed, and therefore, the stiffening effect is lost.

Comparative experiment: PIC-PNIAPAM hybrids (1 mg/mL PIC, 17 mg/mL PNIPAM) was prepared in deionised water (MilliQ) or in 0.5 M NaClO4 following the procedure described above. The sodium perchlorate increases LCSTa and decreases LCSTb, such that now LCSTb>LCSTa and the extreme stiffening effect has disappeared. Result is shown in FIG. 9.

Figure 10:
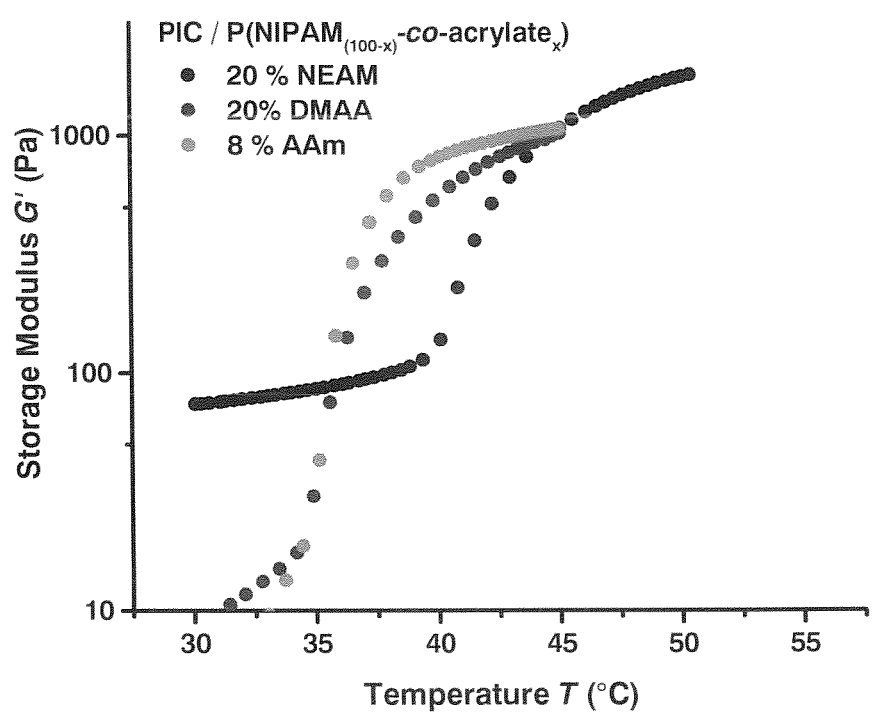
FIG. 10 shows examples of tuning the gelation temperature of the flexible-network by the use of the acrylate comonomers N-ethylacrylamide (NEAM), N,N-dimethylacrylamide (DMAA) and acrylamide (AAm).

Example: Hybrids of PIC (1 mg/mL) and copolymers of NIPAM and N-ethylacrylamide (NEAM), N,N-dimethylacrylamide (DMAA) and acrylamide (AAm) were prepared in an aqueous environment following the procedure described above. NIPAM/NEAM was polymerised in water, NIPAM/DMAA and NIPAM/AAm in aqueous salt solutions (26 mM NaHCO3, 117 mM NaCl). LCSTb and with it the jump in the jump in the storage modulus shift to higher temperature. Results are shown in FIG. 10.

Measurement of persistence length.

For the experimental determination of the persistence length of polymers, single molecule force spectroscopy (SMFS) is used. To do the force experiments, a drop of aqueous polymer solution was put onto the substrate and the cantilever was immersed into the solution. Polymers adhere to the substrate by non-specific physical interactions. By the movement of piezo, the sample was brought into contact with an AFM tip and some polymers would adsorb onto the tip due to nonspecific interactions between the polymer and the tip, producing a connective bridge in-between. During the subsequent separation of the tip and the sample, the polymer chain was stretched and the cantilever would deflect. At the same time, a deflection-extension curve was recorded and converted into a force-extension curve. To extract persistence lengths, the recorded force extension curves semi-flexible polymers were fitted to an Extendable Worm-Like Chain (eWLC) model, whereas the force extension curves flexible polymers were fitted to Freely Joint Chain (FJC) model.

See also: Single Polymer Chain Elongation of Poly(N-isopropylacrylamide) and Poly(acrylamide) by Atomic Force Microscopy; Wenke Zhang, Shan Zou, Chi Wang, and, and Xi Zhang*; The Journal of Physical Chemistry B 2000 104 (44), 10258-10264 DOI: 10.1021/jp000459f.

What is claimed is:

1. A double network hydrogel comprising:
   a. a polymer (A) having a persistence length between 10 and 1000 nm,
   b. a polymer (B) having a persistence length smaller than 1 nm,
   wherein the persistence length is measured at room temperature in an aqueous solution at neutral pH according to single molecule force microscopy measurement,
   wherein polymer (B) has an extended coil conformation at a first condition and a collapsed globular conformation at a second condition,
   wherein the concentration of polymer (B) ranges between 1 and 80 mg/mL,
   wherein the polymer (B) is a temperature responsive (thermoresponsive) polymer having a lower critical solution temperature (LCSTb), whereby the first condition is present at a temperature below LCSTb and the second condition is present at a temperature above the LCSTb,
   wherein the polymer (A) has a lower critical solution temperature (LCSTa),
   wherein the LCSTb is higher than the LCSTa, and
   wherein the LCSTa is between 5° C. and 20° C.

2. The double network hydrogel according to claim 1, wherein polymer (A) is selected from polyisocyanopeptides, DNA, actin, fibrin, intermediate filaments, collagen and cellulose derivatives.

3. The double network hydrogel according to claim 1, wherein polymer (A) is an oligo(alkylene glycol)functionalized poly(isocyanopeptide).

4. The double network hydrogel according to claim 3, wherein polymer (A) is a polymer based on the polymerization of isocyanopeptides which are functionalized with at least 3 ethylene glycol units.

5. The double network hydrogel according to claim 2, wherein the polyisocyanopeptides (PIC) are present at a concentration between 0.25 mg/ml and 3.0 mg/ml.

6. The double network hydrogel according to claim 1, wherein the viscosity average molecular weight of polymer (A) ranges between 200 and 1000 kg/mol (kDalton).

7. The double network hydrogel according to claim 1, wherein polymer (B) is PNIPAM crosslinked with a multifunctional acrylate.

8. The double network hydrogel according to claim 7, wherein the concentration of PNIPAM ranges between 3 and 80 mg/l.

9. A double network hydrogel according to claim 1, wherein polymer (B) is selected from poly(acrylic acid) (PAAc) or poly(2-(dimethylamino)ethylethyl acrylate) (PDMA), copolymerized with acrylamide.

10. A process for making the double network hydrogel according to claim 1, comprising the steps of:
  a. providing an aqueous solution of polymer (A) at a temperature below a lower critical solution temperature of polymer (A) (LCSTa);
  b. providing monomers B to be polymerized to polymer (B) having a LCSTb;
  c. mixing the aqueous solution of polymer (A) with monomers (B) and subsequently heating the mixture to a temperature above the LCSTa and below the LCSTb to provide a hydrogel comprising polymer (A) and monomers (B);
  d. inducing polymerization of monomers (B) at a temperature above the LCSTa and below the LCSTb to provide a double network hydrogel;
  e. wherein polymer (A) is a polymer as defined above in claim 1 and
  f. wherein polymer (B) is a polymer as defined above in claim 1.

11. A method of using a hydrogel, comprising the step of: culturing cells with the double network hydrogel of claim 1.

12. A coating, comprising: the double network hydrogel according to claim 1.

13. The double network hydrogel according to claim 5, wherein the polyisocyanopeptides (PIC) have the LCSTa between 10° C. and 20° C.

14. The double network hydrogel according to claim 6, wherein the viscosity average molecular weight of polymer (A) ranges between 250 and 700 kg/mol.

15. The double network hydrogel according to claim 7, wherein polymer (B) is PNIPAM crosslinked with N,N'-methylenebisacrylamide (MBAA).

16. The double network hydrogel according to claim 9, wherein polymer (B) is PAAc with acrylamide, crosslinked with N,N'-methylenebisacrylamide (MBAA), wherein the concentration of polymer (B) ranges between 3 and 30 mg/mL, and wherein the LCSTb is at least 2° C. higher than the LCSTa.

17. The double network hydrogel according to claim 1, wherein the LCSTb is at least 2° C. higher than the LCSTa.

18. The double network hydrogel according to claim 17, wherein the LCSTb ranges between 20° C. and 40° C., and is at least 4° C. higher than the LCSTa.

\* \* \* \* \*